(12) United States Patent
Fujii

(10) Patent No.: US 7,438,684 B2
(45) Date of Patent: Oct. 21, 2008

(54) ULTRASONIC DIAGNOSTIC APPARATUS FOR CONTROLLING THE SURFACE TEMPERATURE OF A PROBE

(75) Inventor: Kiyoshi Fujii, Yokohama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 21 days.

(21) Appl. No.: 10/560,846

(22) PCT Filed: Jun. 30, 2004

(86) PCT No.: PCT/JP2004/009594

§ 371 (c)(1),
(2), (4) Date: Dec. 15, 2005

(87) PCT Pub. No.: WO2005/002445

PCT Pub. Date: Jan. 13, 2005

(65) Prior Publication Data
US 2006/0241426 A1 Oct. 26, 2006

(30) Foreign Application Priority Data
Jul. 4, 2003 (JP) .............................. 2003-191700

(51) Int. Cl.
*A61B 8/00* (2006.01)
*G01K 11/22* (2006.01)
(52) U.S. Cl. ....................... 600/437; 374/119
(58) Field of Classification Search ............. 600/437, 600/459
See application file for complete search history.

(56) References Cited

U.S. PATENT DOCUMENTS

| 4,469,450 | A | * | 9/1984 | DiVincenzo | ................ | 374/119 |
|---|---|---|---|---|---|---|
| 4,865,042 | A | * | 9/1989 | Umemura et al. | ........... | 600/439 |
| 5,360,268 | A | * | 11/1994 | Hayashi et al. | ............. | 374/117 |
| 5,776,065 | A | * | 7/1998 | Mehmanpazir et al. | ..... | 600/437 |
| 5,961,465 | A | * | 10/1999 | Kelly et al. | ................. | 600/459 |
| 6,083,165 | A | * | 7/2000 | Kaplan | ....................... | 600/438 |
| 6,663,578 | B1 | * | 12/2003 | Peszynski et al. | .............. | 601/2 |
| 7,156,551 | B2 | * | 1/2007 | Ramamurthy et al. | ....... | 374/119 |
| 2005/0215892 | A1 | * | 9/2005 | Emery et al. | ................ | 600/437 |

FOREIGN PATENT DOCUMENTS

| JP | 5-49642 | 3/1993 |
|---|---|---|
| JP | 7-178081 | 7/1995 |
| JP | 7-178089 | 7/1995 |
| JP | 7-265315 | 10/1995 |
| JP | 10-33529 | 2/1998 |
| JP | 10-127632 | 5/1998 |
| JP | 2000-5165 | 1/2000 |
| JP | 2000-107177 | 4/2000 |
| JP | 2001-321377 | 11/2001 |

* cited by examiner

*Primary Examiner*—Eric F Winakur
*Assistant Examiner*—Helene Bor
(74) *Attorney, Agent, or Firm*—Pearne & Gordon LLP

(57) ABSTRACT

A technology is disclosed for holding the test subject contact surface temperature below a predetermined value without providing a temperature sensor or setting ultrasonic wave output excessively low and, according to this technology, reflex time t1, which passes through oil 6, is reflected by the inner surface of window 5, and is returned via oil, and reflex time t2, which passes through the window, is reflected by the outer surface of the window, and returned via window or oil, are detected, sound velocity of window=(thickness of window×2)/ $(t2-t1)$ is measured, and the surface temperature of the window is detected from this measured sound velocity.

4 Claims, 4 Drawing Sheets

ULTRASONIC DIAGNOSTIC APPARATUS FOR CONTROLLING THE SURFACE TEMPERATURE OF A PROBE

TECHNICAL FIELD

The present invention relates to an ultrasonic diagnostic apparatus for controlling the test subject contact surface temperature of an ultrasonic probe.

BACKGROUND ART

Because the surface of an ultrasonic probe comes into direct contact with the patient, legal regulations exist such that the surface is below a predetermined temperature (for example, 43° C.) in order to avoid injury such as burns to the patient. As Prior Example 1, a method for controlling ultrasonic wave output by providing a temperature sensor within a probe, for example, is proposed, as shown in Patent Documents 1 and 2, below. In addition, as Prior Example 2, a method for controlling the applied voltage of a probe by software and hardware such that surface temperature does not exceed the regulation value by measuring the relation between the applied voltage of the probe and surface temperature beforehand, in place of providing a temperature sensor, for example, is proposed, as shown in Patent Reference 3, below. Patent Reference 1: Japanese Patent Application Publication No. H7-265315 (FIG. 1, Paragraph 0008) Patent Reference 2: Japanese Patent Application Publication No. 2001-321377 (FIG. 1, Paragraph 0026) Patent Reference 3: Japanese Patent Application Publication No. 2000-5165 (FIG. 1, Paragraph 0020)

However, in the foregoing Prior Example 1 which uses temperature sensor, there is a problem in that it becomes more expensive due to the temperature sensor and, in addition, there is a problem in that the probe surface temperature, which is the test subject contact surface temperature, cannot be measured accurately depending on the arrangement position (Issue 1).

In addition, in the foregoing Prior Example 2 wherein surface temperature is controlled by software and hardware, there is a problem in that the surface temperature sometimes exceeds regulation value due to bugs in the software, runaway software, hardware malfunction and the like. Furthermore, in practice, when ultrasonic waves are received consecutively, the surface temperature gradually rises according to the specific heat of the probe window or internal fluid, and even if the regulation value is not exceeded suddenly, there is a problem in that the sensitivity of ultrasound image is poor because ultrasonic wave output is set excessively low in Prior Example 2 (Issue 2).

DISCLOSURE OF THE INVENTION

In light of the foregoing Issues 1 and 2, the object of the present invention is to provide an ultrasonic diagnostic apparatus which can hold the test subject contact surface temperature below a predetermined value without providing a temperature sensor or setting ultrasonic wave output excessively low, thereby preventing low-temperature burn injuries.

In order to achieve the foregoing object, the present invention comprises:

a sound velocity calculation means for calculating the sound velocity of ultrasonic waves based on the difference between the reflex time of ultrasonic wave reflected from the inner surface of a window in contact with the test subject and the reflex time of ultrasonic wave reflected from the outer surface of the window and the thickness of the window;

a temperature calculation means for calculating the temperature of the window, based on sound velocity calculated by the sound velocity calculation means; and an ultrasonic wave output control means for controlling ultrasonic wave output, based on temperature calculated by the temperature calculation means.

Because the temperature of the window in contact with the test subject can be detected by the foregoing construction, the test subject contact surface temperature can be held below a predetermined value without providing a temperature sensor or setting ultrasonic wave output excessively low, thereby preventing low-temperature burn injuries.

In addition, in order to achieve the foregoing objective, the present invention comprises:

a sound velocity calculation means for calculating the sound velocity of ultrasonic waves based on the reflex time of ultrasonic wave passing through fluid wherein sonic elements vibrate and reflected from the inner surface of a window in contact with the test subject and the thickness of the fluid;

a temperature calculation means for calculating the temperature of the fluid based on the sound velocity calculated by the sound velocity calculation means; and an ultrasonic wave output control means for controlling ultrasonic wave output based on temperature calculated by the temperature calculation means.

Because the temperature of the window can be detected by the foregoing construction, the test subject contact surface temperature can be held below a predetermined value without providing a temperature sensor or setting ultrasonic wave output excessively low, thereby preventing low-temperature burn injuries.

Furthermore, the present invention further comprises:

a memory means for storing the thickness of the window and the thickness of the fluid obtained by detecting the reflex times of ultrasonic waves under a certain temperature beforehand and performing calibrations respectively, for the window and the fluid; and, wherein the sound velocity calculation means calculates the sound velocity of ultrasonic waves based on the thickness of the window or the thickness of the fluid stored by the memory means.

Errors in the measured temperatures due to dispersion in the thickness of the window and the thickness of the fluid can be reduced, and temperature detection of a higher accuracy can be performed.

BEST MODE FOR CARRYING OUT THE INVENTION

Descriptions are hereinafter given of the embodiments of the present invention with reference to the drawings.

Figure 1A:
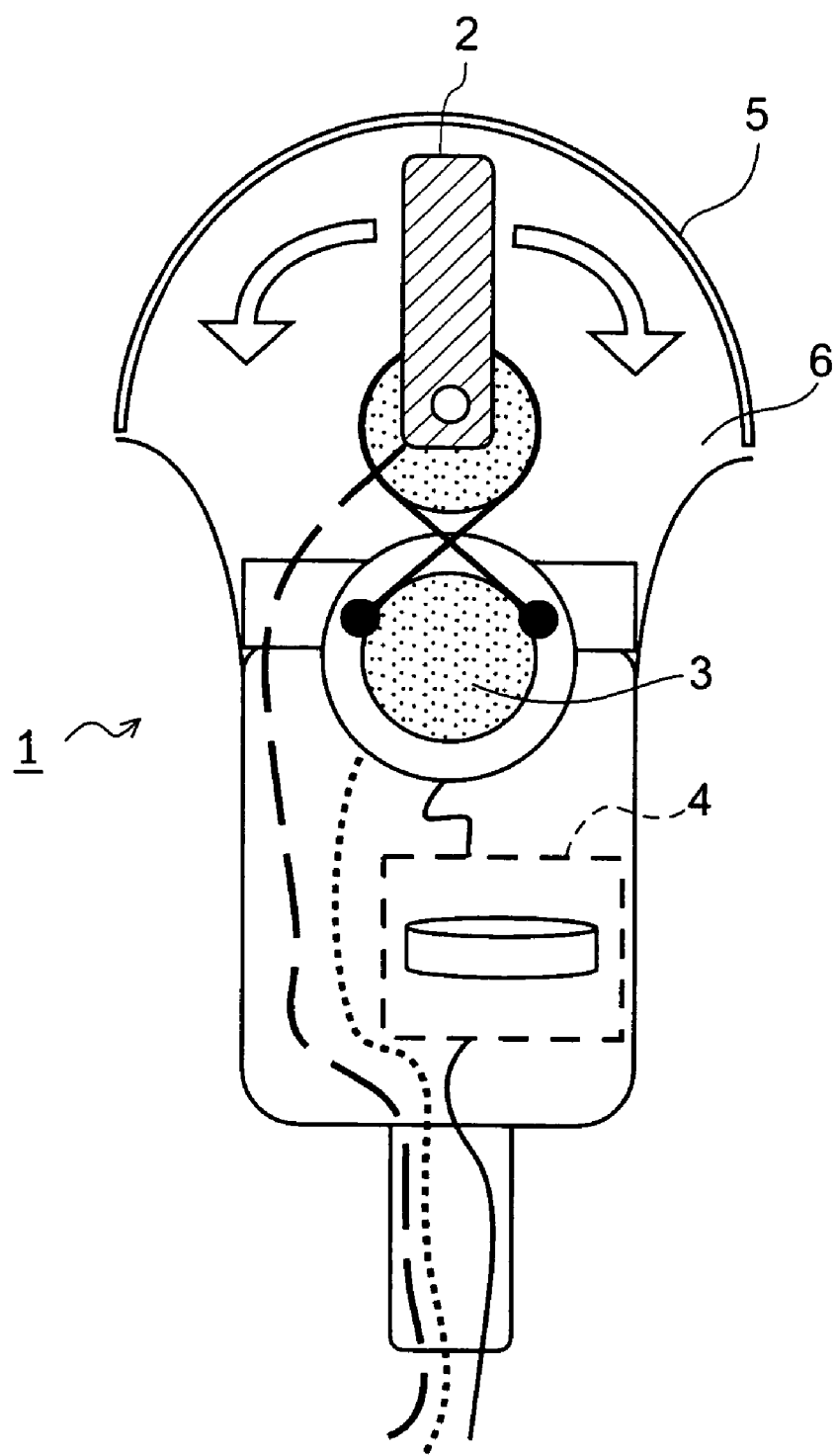
FIG. 1A is an internal configuration diagram of an ultrasonic probe according to the present invention when viewed from the side.
Figure 1B:
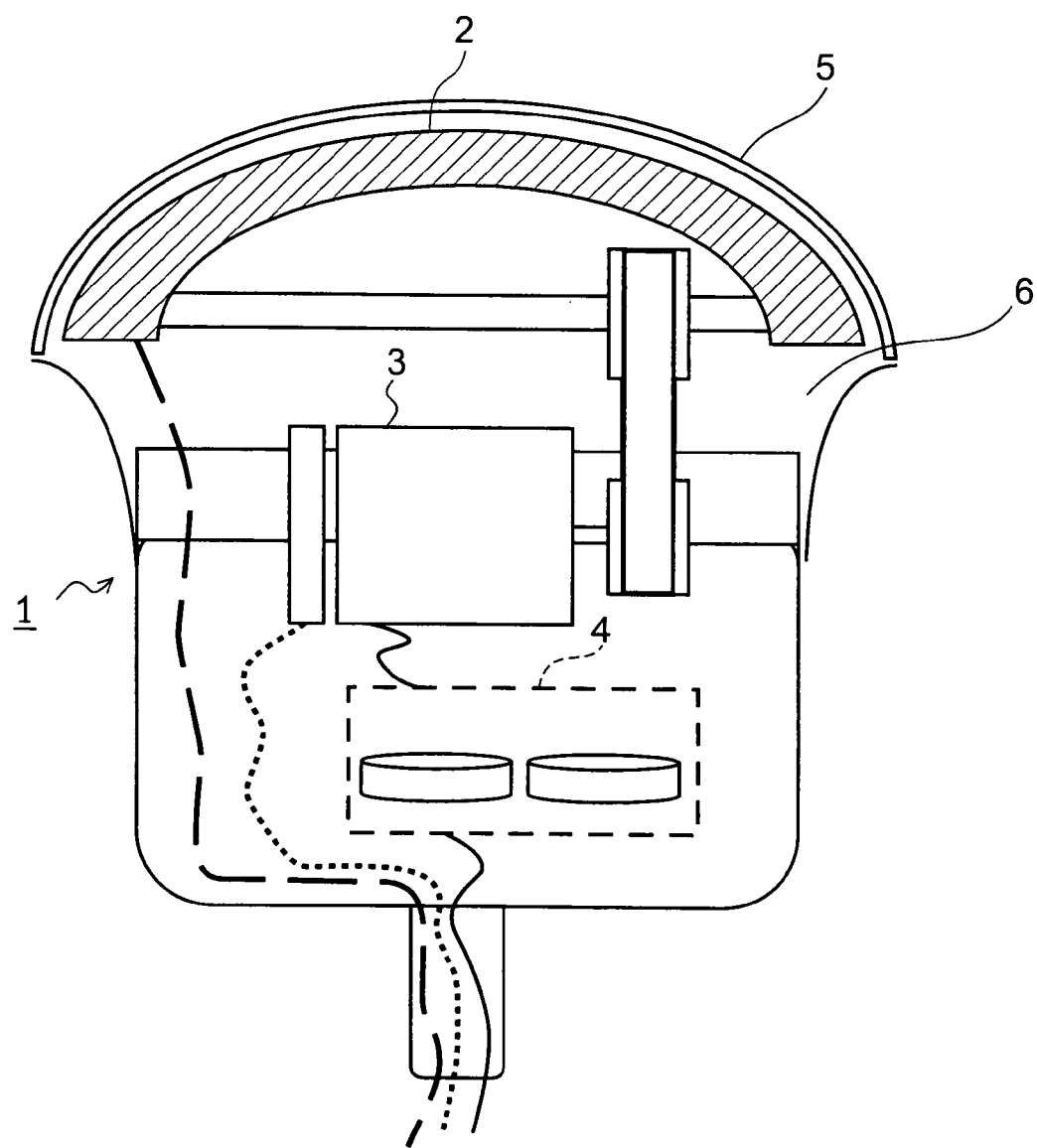
FIG. 1B is a an internal configuration diagram of the ultrasonic probe according to the present invention when viewed from the front.
Figure 2:
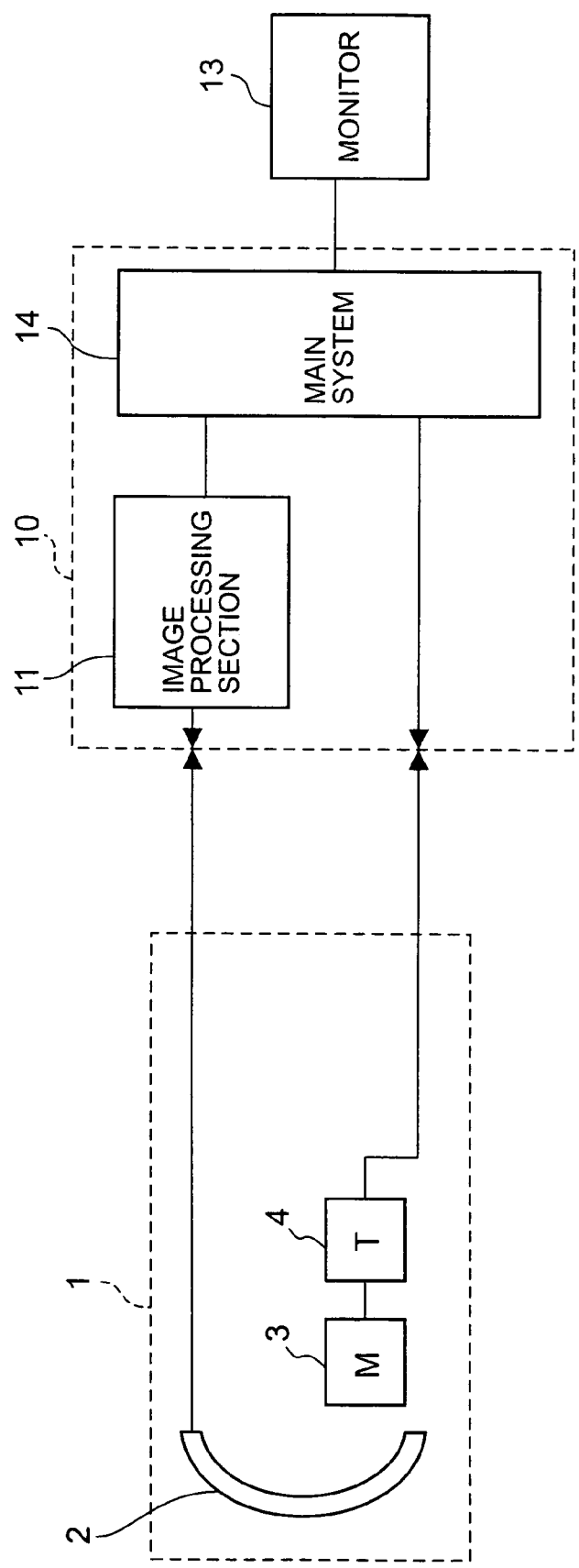
FIG. 2 is a block diagram showing one embodiment of an ultrasonic diagnosis device according to the present invention.

FIG. 1A shows the internal configuration of an ultrasonic probe 1 according to the present invention when viewed from the side, and FIG. 1B shows the internal configuration of the ultrasonic probe 1 when viewed from the front. In FIG. 1A and FIG. 1B, the ultrasonic probe 1 is connected to an ultrasonic diagnostic apparatus main unit 10, shown in FIG. 2, via cable such as to enable connection and detachment. In the inner part which is separated from the outer part by window 5 at the tip of the ultrasonic probe 1, an arc-shaped sonic element 2 is supported by an ultrasonic motor (M) 3 such as to enable back and forth rotation within oil 6 in the direction perpendicular to the arc direction. Ultrasonic motor 3 is driven by providing driving electrical power from the ultrasonic diagnostic apparatus main unit 10, shown in FIG. 2, via a two-phase transformer (T) 4. Then, as shown in FIG. 2, the output of sonic element 2 is transmitted to the ultrasonic diagnostic apparatus main unit 10, processed by an image processing section 11 into a three-dimensional image in the arc direction, scanning direction and depth direction of the sonic element 2, and this three-dimensional image is shown on monitor 13.

Incidentally, the attribute of "temperature-sound velocity of polymethylpentene as window 5 and 1.3 butanediol as oil 6 is as shown in Table 1 and the graph in FIG. 3, below:

TABLE 1

|  | 10 | 20 | 30 | 40° C. |
|---|---|---|---|---|
| Window 5 | 1984 | 1929 | 1870 | 1810 m/s |
| Oil 6 | 1583 | 1555 | 1528 | 1498 m/s |

Figure 4A:
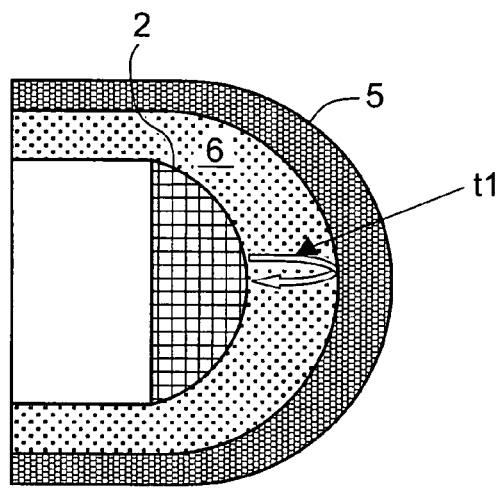
FIG. 4A is a schematic diagram showing reflection due to the inner surface of the window in FIG. 1A and 1B.
Figure 4B:
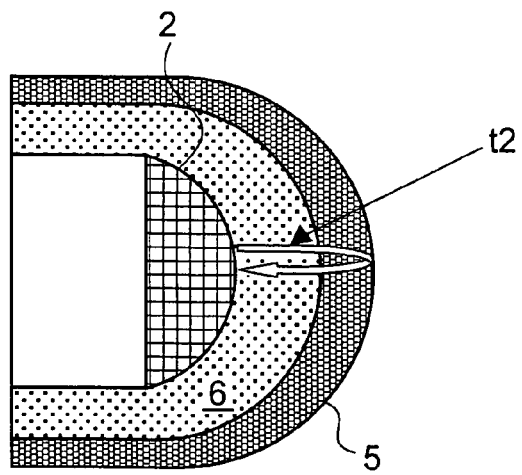
FIG. 4B is a schematic diagram showing reflection due to the outer surface of the window in FIG. 1A and FIG. 1B.

In addition, if ultrasonic pulses are outputted from the sonic element 2 when the ultrasonic probe 1 is not touching the test subject, they pass through oil 6, are reflected by the inner surface of window 5, and returns via oil 6, as shown in FIG. 4A, and therefore, are received by sonic element 2 after time t1 has passed from output. Furthermore, on the other hand, they pass through window 5, are reflected by the outer surface of window 5, and returns via window 5 or oil 6, as shown in FIG. 4B, and therefore, are received by sonic element 2 after time t2 has passed from output.

Figure 3:
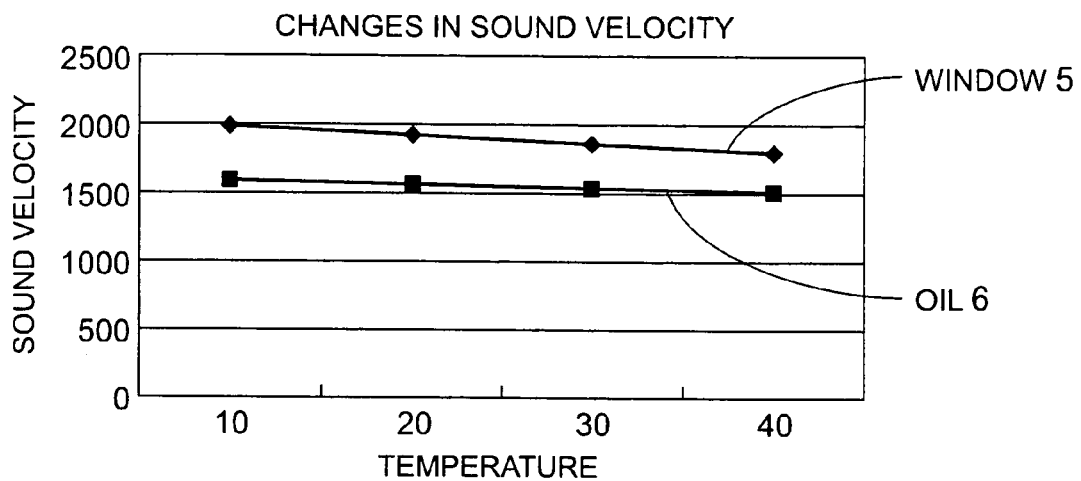
FIG. 3 is a graph showing the "temperature-sound velocity" attributes of the window in FIG. 1 and oil.

Consequently, sound velocity of window 5 =(thickness of window 5×2)/(t2−t1) is measured by main system 14 within the ultrasonic diagnostic apparatus main unit 10, and the surface temperature of window 5 can be detected from this measured sound velocity with reference to a graph such as that shown in FIG. 3. Then, if this temperature exceeds the predetermined value, the output of ultrasonic waves can be terminated or reduced.

In addition, in a three-dimensional device which rotates sonic element 2, such as this embodiment shown in the Figures, oil 6 is agitated and there is little difference between the temperatures of window 5 and oil 6, and therefore, by measuring sound velocity of oil 6=(thickness of oil 6×2)/t1, the surface temperature of window 5 can be detected indirectly.

Here, errors in measured temperatures occur due to dispersions between "thickness of window 5" and "thickness of oil 6". Therefore, by providing a memory which stores "thickness of window 5" and "thickness of oil 6," obtained by measuring the ultrasonic propagation time of window 5 and oil 6 for each ultrasonic probe 1, when the ultrasonic probe 1 is in an assembled state, under a certain temperature beforehand and performing calibration, within the ultrasonic probe 1 and calculating the sound velocity of ultrasonic waves based on the "thickness of window 5" and "thickness of oil 6" which are stored in this memory, errors in measured temperature due to dispersions between "thickness of window 5" and "thickness of oil 6" can be reduced and temperature detection of a higher accuracy can be performed.

Although the detection of sound velocity and temperature is performed on the ultrasonic diagnostic apparatus main unit 10 side in the foregoing embodiment, it can also be performed on the ultrasonic probe 1 side, and in this case, the existing ultrasonic diagnostic apparatus main unit 10 side can have a fail safe function. In addition, although a three-dimensional ultrasonic diagnostic apparatus is given as an example in the foregoing embodiment, it can be applied to a two-dimensional ultrasonic diagnostic apparatus, as well. Here, if the temperature exceeds the predetermined value when the user is using a three-dimensional ultrasonic diagnostic apparatus in two-dimensional mode (ultrasonic motor 3 is in a stop-state), temperature rise can be controlled by agitating oil 6 by rotating ultrasonic motor 3, without stopping or reducing the output of ultrasonic waves, and therefore, the amount of time in an high-output state can be extended.

INDUSTRIAL APPLICABILITY

According to the present invention as described above, because the temperature of the window which comes into contact with the test subject can be detected, the test subject contact surface temperature can be held below a predetermined value without providing a temperature sensor or setting ultrasonic wave output excessively low, thereby preventing low-temperature burn injuries.

In addition, according to other embodiments of the present invention, because the temperature of the window can be detected, the test subject contact surface temperature can be held below a predetermined value without providing a temperature sensor or setting ultrasonic wave output excessively low, thereby preventing low-temperature burn injuries.

Furthermore, according to other embodiments of the present invention, errors in the measured temperatures due to dispersion in the thickness of the window and the thickness of the fluid can be reduced, and temperature detection of a higher accuracy can be performed.

The invention claimed is:

1. An ultrasonic diagnostic apparatus, comprising:
   an ultrasonic probe including a window configure for contact with a test subject, the window having an inner surface and an outer surface;
   a sound velocity calculation means for calculating the sound velocity of ultrasonic waves based on the difference between the reflex time of ultrasonic wave reflected from the inner surface of the window and the reflex time of ultrasonic wave reflected from the outer surface of the window and the thickness of the window;
   a temperature calculation means for calculating the temperature of the window based on sound velocity calculated by the sound velocity calculation means; and
   an ultrasonic wave output control means for controlling ultrasonic wave output based on temperature calculated by the temperature calculation means.

2. The ultrasonic diagnostic apparatus according to claim 1, further comprising:
   a memory means for storing the thickness of said window and the thickness of said fluid obtained by detecting said reflex times of ultrasonic waves under a certain temperature beforehand and performing calibrations respectively, for the window and the fluid; and, wherein said sound velocity calculation means calculates the sound velocity of ultrasonic waves based on the thickness of the window or the thickness of the fluid stored by the memory means.

3. An ultrasonic diagnostic apparatus, comprising:

an ultrasonic probe including a window configure for contact with a test subject, the window having an inner surface;

a sound velocity calculation means for calculating the sound velocity of ultrasonic waves based on the reflex time of ultrasonic wave passing through fluid wherein sonic elements vibrate and reflected from the inner surface of the window, and the thickness of the fluid;

a temperature calculation means for calculating the temperature of the fluid based on the sound velocity calculated by the sound velocity calculation means; and an ultrasonic wave output control means for controlling ultrasonic wave output based on temperature calculated by the temperature calculation means.

4. The ultrasonic diagnostic apparatus according to claim 3, further comprising:

a memory means for storing the thickness of said window and the thickness of said fluid obtained by detecting said reflex times of ultrasonic waves under a certain temperature beforehand and performing calibrations respectively, for the window and the fluid; and, wherein said sound velocity calculation means calculates the sound velocity of ultrasonic waves based on the thickness of the window or the thickness of the fluid stored by the memory means.

\* \* \* \* \*